United States Patent
Lee et al.

(10) Patent No.: US 11,660,142 B2
(45) Date of Patent: May 30, 2023

(54) METHOD FOR GENERATING SURGICAL SIMULATION INFORMATION AND PROGRAM

(71) Applicant: HUTOM CO., LTD., Seoul (KR)

(72) Inventors: Jong Hyuck Lee, Seongnam-si (KR); Woo Jin Hyung, Seoul (KR); Hoon Mo Yang, Gunpo-si (KR); Ho Seung Kim, Yongin-si (KR)

(73) Assignee: HUTOM CO., LTD., Seoul (KR)

(*) Notice: Subject to any disclaimer, the term of this patent is extended or adjusted under 35 U.S.C. 154(b) by 305 days.

(21) Appl. No.: 16/913,959

(22) Filed: Jun. 26, 2020

(65) Prior Publication Data

US 2020/0360089 A1 Nov. 19, 2020

Related U.S. Application Data

(63) Continuation of application No. PCT/KR2018/013947, filed on Nov. 15, 2018.

(30) Foreign Application Priority Data

Dec. 28, 2017 (KR) .......................... 10-2017-0182888

(51) Int. Cl.
*A61B 34/10* (2016.01)
*G06T 17/20* (2006.01)
(Continued)

(52) U.S. Cl.
CPC .............. *A61B 34/10* (2016.02); *A61B 90/36* (2016.02); *G06N 20/00* (2019.01);
(Continued)

(58) Field of Classification Search
CPC ... A61B 34/10; A61B 90/36; A61B 2034/105; A61B 2034/107; A61B 2090/364;
(Continued)

(56) References Cited

U.S. PATENT DOCUMENTS 10,130,429 B1* 11/2018 Weir ...................... A61B 34/76
11,116,574 B2* 9/2021 Haider ............... A61B 17/1675
(Continued)

FOREIGN PATENT DOCUMENTS

CN         102282527 A      12/2011
DE   10 2009 049819 A1      5/2011
(Continued)

OTHER PUBLICATIONS

International Search Report issued in PCT/KR2018/013947; dated Feb. 12, 2019.
(Continued)

*Primary Examiner* — Phong X Nguyen
(74) *Attorney, Agent, or Firm* — Studebaker & Brackett PC

(57) ABSTRACT

A method for creating surgical simulation information by a computer includes creating a virtual body model corresponding to a body state of a patient for surgery, simulating a specific surgical process on the virtual body model to obtain virtual surgical data, dividing the virtual surgical data into minimum surgical operation units, each unit representing one specific operation, and creating cue sheet data composed of the minimum surgical operation units, wherein the cue sheet data represents the specific surgical process.

9 Claims, 6 Drawing Sheets

(51) Int. Cl.
  *A61B 90/00* (2016.01)
  *G06N 20/00* (2019.01)
(52) U.S. Cl.
  CPC ... *A61B 2034/105* (2016.02); *A61B 2034/107* (2016.02); *A61B 2090/364* (2016.02)
(58) Field of Classification Search
  CPC . A61B 34/30; A61B 90/361; A61B 2034/101; A61B 2090/502; A61B 2034/252; A61B 2034/256; A61B 2034/2065; A61B 34/20; G06N 20/00; G06T 17/20
  See application file for complete search history.

(56) References Cited

U.S. PATENT DOCUMENTS

| | | | | |
|---|---|---|---|---|
| 2007/0106633 | A1* | 5/2007 | Reiner | G06Q 10/0633 |
| 2013/0173223 | A1* | 7/2013 | Teller | G06N 20/00 |
| | | | | 703/1 |
| 2014/0081659 | A1 | 3/2014 | Nawana et al. | |
| 2014/0129200 | A1* | 5/2014 | Bronstein | G06T 17/00 |
| | | | | 703/11 |
| 2014/0133727 | A1* | 5/2014 | Oktay | G06T 7/33 |
| | | | | 382/131 |
| 2016/0249989 | A1* | 9/2016 | Devam | A61B 5/021 |
| | | | | 345/633 |
| 2017/0007327 | A1* | 1/2017 | Haider | A61B 17/154 |
| 2017/0079719 | A1* | 3/2017 | Warner | G06T 17/00 |
| 2018/0032841 | A1* | 2/2018 | Kluckner | G06N 3/006 |
| 2018/0116724 | A1* | 5/2018 | Gmeiner | B29C 35/02 |
| 2018/0357514 | A1* | 12/2018 | Zisimopoulos | G06V 10/26 |
| 2018/0360543 | A1* | 12/2018 | Roh | G16H 20/40 |
| 2018/0368930 | A1* | 12/2018 | Esterberg | A61B 34/76 |
| 2019/0365475 | A1* | 12/2019 | Krishnaswamy | A61B 17/3403 |
| 2020/0360089 | A1* | 11/2020 | Lee | A61B 34/10 |
| 2021/0058485 | A1* | 2/2021 | Devam | H04L 67/60 |
| 2022/0100792 | A1* | 3/2022 | Lee | G06N 20/00 |
| 2022/0192611 | A1* | 6/2022 | Kohli | A61B 6/461 |

FOREIGN PATENT DOCUMENTS

| | | |
|---|---|---|
| EP | 1 769 771 A1 | 4/2007 |
| JP | 2005-124824 A | 5/2005 |
| KR | 10-2005-0048438 A | 5/2005 |
| KR | 10-2010-0124638 A | 11/2010 |
| KR | 10-2012-0111871 A | 10/2012 |
| KR | 10-1302595 B1 | 8/2013 |
| KR | 10-2015-0113929 A | 10/2015 |
| KR | 10-2016-0092425 A | 8/2016 |

OTHER PUBLICATIONS

The extended European search report issued by the European Patent Office dated Jul. 22, 2021, which corresponds to European Patent Appliation No. 18894558.8-1122 and is related to U.S. Appl. No. 16/913,959.

An Office Action mailed by the Korean Intellectual Property Office dated Mar. 31, 2021, which corresponds to Korean Patent Application No. 10-2019-0005210 and is related to U.S. Appl. No. 16/913,959.

An Office Action mailed by China National Intellectual Property Administration dated Dec. 30, 2022, which corresponds to Chinese Patent Application No. 201880088984.X and is related to U.S. Appl. No. 16/913,959.

* cited by examiner

METHOD FOR GENERATING SURGICAL SIMULATION INFORMATION AND PROGRAM

CROSS-REFERENCE TO RELATED APPLICATIONS

The present application is a continuation of International Patent Application No. PCT/KR2018/013947, filed on Nov. 15, 2018, which is based upon and claims the benefit of priority to Korean Patent Application No. 10-2017-0182888, filed on Dec. 28, 2017. The disclosures of the above-listed applications are hereby incorporated by reference herein in their entirety.

BACKGROUND

Embodiments of the inventive concept described herein relate to a method and a program for creating surgical simulation information.

There is a need to develop a scheme capable of providing information to assist a surgeon in a surgical process. In order to provide the information to assist with the surgery, actions of the surgery must be recognized.

Conventionally, in order to design a scenario for optimizing the surgical process, a medical image that is previously captured is referred to or an advice from a highly skilled surgeon is referred. However, it is difficult to determine unnecessary processes only based on the medical image, and the advice of the experienced surgeon is not customized to a specific patient.

Therefore, the medical image or the advice of the skilled surgeon may not be utilized as auxiliary means for optimizing the surgical process for a surgery target patient as a surgery target.

Accordingly, development of a method for minimizing unnecessary processes in performing the surgery using a 3D medical image (for example, virtual images of 3D surgical tool movements and internal organ changes caused by the movement of the tool) to optimize the surgical process, and providing surgery assisting information based on the optimized surgical process is required.

Further, recently, deep learning has been widely used for analysis of medical images. Deep learning is defined as a set of machine-learning algorithms that attempt high-level abstractions (abstracting of key content or functions in a large amount of data or complex data) via a combination of several nonlinear transformation schemes. Deep learning may be largely considered as a field of machine learning that teaches a human mindset to a computer.

SUMMARY

Embodiments of the inventive concept provide a method and a program for creating surgical simulation information.

Purposes that the inventive concept intends to achieve are not limited to those mentioned above. Other purposes as not mentioned will be clearly understood by those skilled in the art from following descriptions.

According to an exemplary embodiment, a method for creating surgical simulation information by a computer includes creating a virtual body model corresponding to a body state of a patient for surgery, simulating a specific surgical process on the virtual body model to obtain virtual surgical data, dividing the virtual surgical data into minimum surgical operation units, each unit representing one specific operation, and creating cue sheet data composed of the minimum surgical operation units, wherein the cue sheet data represents the specific surgical process.

Further, the dividing of the virtual surgical data into the minimum surgical operation units may include recognizing whether a specific event has occurred based on the virtual surgical data, and recognizing the minimum surgical operation units based on the specific event, wherein the specific event includes change in at least one of surgical tool and a surgery target portion included in the virtual surgical data.

Further, the recognizing of whether the specific event has occurred may include recognizing whether the event has occurred, based on change in an operation of the surgical tool, recognizing whether the event has occurred, based on change in a state of the surgery target portion, or recognizing whether the event has occurred, based on whether change in a state of the surgery target portion occurs as change in an operation of the surgical tool occurs.

Further, the creating of the cue sheet data may include sequentially combining the minimum surgical operation units in a corresponding manner to the specific surgical process, thereby to create the cue sheet data.

Further, the creating of the virtual body model may include obtaining a medical image including a surgery target portion of the patient, and 3D-modeling the obtained medical image to create the virtual body model.

Further, the creating of the virtual body model may further include obtaining an actual surgery posture of the patient, and 3D-modeling the virtual body model by correcting the medical image based on the actual surgery posture.

Further, the method may further include determining whether the created cue sheet data is optimized.

Further, the determining of whether the created cue sheet data is optimized may further include providing surgical guide data based on the cue sheet data determined to be optimized.

Further, the determining of whether the created cue sheet data is optimized may include obtaining optimized cue sheet data, and comparing the created cue sheet data with the optimized cue sheet data.

Further, the obtaining of the optimized cue sheet data may include obtaining one or more to-be-learned cue sheet data, performing reinforcement learning using the one or more to-be-learned cue sheet data, and obtaining the optimized cue sheet data based on the reinforcement learning result.

According to an exemplary embodiment, a computer program is stored in a computer-readable storage medium, wherein the computer program is configured to perform the method as defined above in combination with a computer as hardware.

According to an exemplary embodiment, a device includes a memory for storing one or more instructions, and a processor configured to execute the one or more instructions stored in the memory, wherein the processor executes the one or more instructions to create a virtual body model corresponding to a body state of a patient for surgery, simulate a specific surgical process on the virtual body model to obtain virtual surgical data, divide the virtual surgical data into minimum surgical operation units, each unit representing one specific operation, and create cue sheet data composed of the minimum surgical operation units, wherein the cue sheet data represents the specific surgical process.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
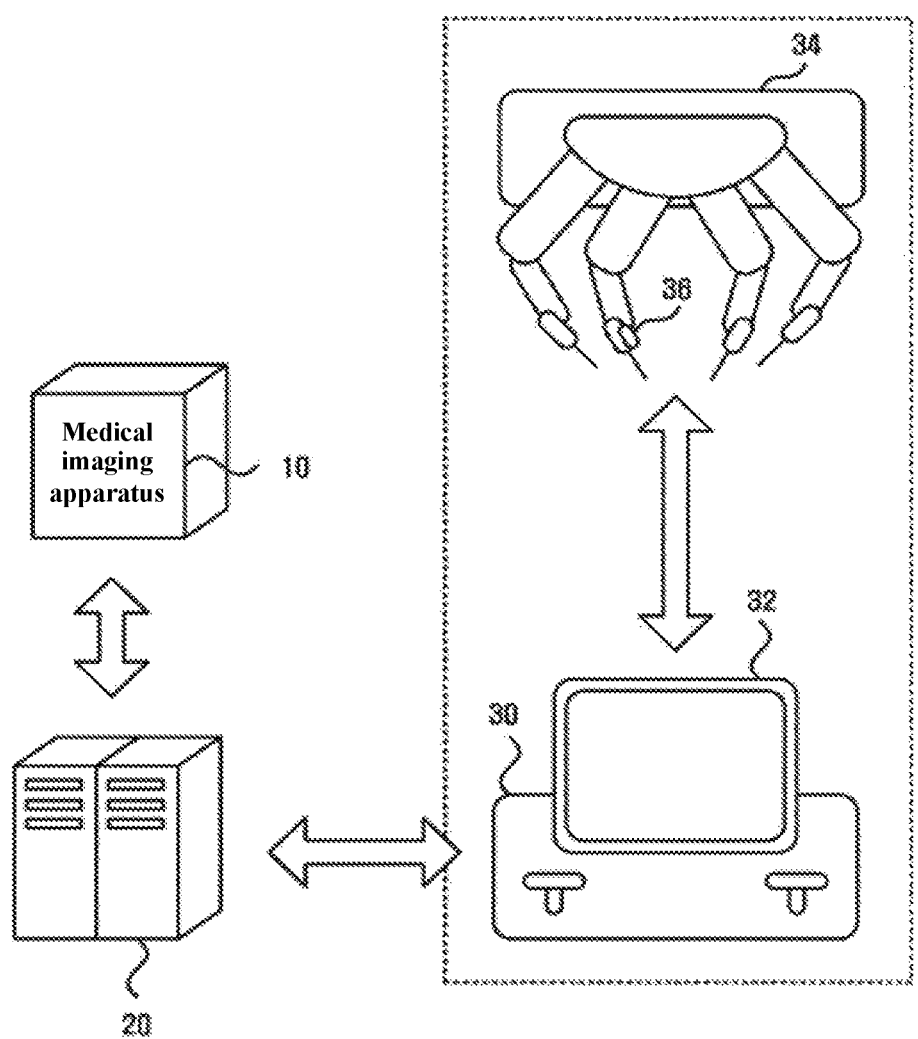
FIG. 1 is a view showing a robot-based surgery system according to a disclosed embodiment.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to inform merely fully those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A term "unit" or "module" used herein means software or a hardware component such as FPGA, or ASIC. The "unit" or "module" performs a predetermined role. However, the "unit" or "module" is not meant to be limited to the software or the hardware. The "unit" or "module" may be configured to reside in an addressable storage medium and may be configured to execute one or more processors. Thus, in an example, the "unit" or "module" includes components such as software components, object-oriented software components, class components and task components, processes, functions, attributes, procedures, subroutines, segments of a program code, drivers, firmware, a microcode, circuitry, data, database, data structures, tables, arrays and variables. Functionality provided within the components and the "units" or "modules" may be combined into a smaller number of components and "units" or "modules" or may be further divided into additional components and "units" or "modules".

As used herein, a term "image" refers to multi-dimensional data composed of discrete image elements (e.g., pixels in a 2D image and voxels in a 3D image). For example, the image may include a medical image of an object obtained by a CT imaging apparatus.

As used herein, the term "object" may be a person or an animal, or a portion or an entirety of a person or animal. For example, the object may include at least one of organs such as a liver, a heart, a uterus, a brain, a breast, and an abdomen, and a blood vessel.

As used herein, a term "user" may be a surgeon, a nurse, a clinical pathologist, a medical image expert, etc. as a medical expert, may be a technician repairing a medical apparatus. However, the present disclosure is not limited thereto.

As used herein, a term "medical image data" refers to a medical image that is captured by a medical imaging apparatus, and includes all medical images that may represent a body of an object in a 3D modelling manner. The "medical image data" may include a computed tomography (CT) image, a magnetic resonance imaging (MRI) image, a positron emission tomography (PET) image, etc.

As used herein, a term "virtual body model" refers to a model created in a conforming manner to an actual patient's body based on the medical image data. The "virtual body model" may be created by modeling the medical image data in a three dimensions manner or by correcting the modeled data to be adapted to an actual surgery situation.

As used herein, a term "virtual surgical data" means data including rehearsal or simulation action performed on the virtual body model. The "virtual surgical data" may be image data of rehearsal or simulation performed on the virtual body model in a virtual space or may be data in which a surgical operation performed on the virtual body model is recorded.

As used herein, a term "actual surgery data" refers to data obtained as a medical staff performs actual surgery. The "actual surgery data" may be image data obtained by imaging a surgery target portion in an actual surgical process, or may be data in which a surgical operation performed in the actual surgical process is recorded.

As used herein, a term "detailed surgical operation" means a minimum unit of a surgical operation as divided according to specific criteria.

As used herein, a term "cue sheet data" refers to data in which detailed surgical operations into which a specific surgical process is divided are recorded in order.

As used herein, a term "to-be-executed cue sheet data" refers to cue sheet data obtained based on the virtual surgical data obtained via simulation by the user.

As used herein, a term "training virtual surgical cue sheet data" is included in the to-be-executed cue sheet data, and means cue sheet data created based on the virtual surgical data obtained via surgery simulation by the user.

As used herein, a term "referenced virtual surgical cue sheet data" refers to cue sheet data about virtual surgery performed by a specific medical person for construction of to-be-learned big data or surgery process guidance.

As used herein, a term "optimized cue sheet data" means cue sheet data about an optimized surgical process in terms of a surgery time or prognosis.

As used herein, a term "to-be-learned cue sheet data" means cue sheet data used for learning for optimized cue sheet data calculation.

As used herein, a term "surgery guide data" means data used as guide information during actual surgery.

As used herein, a term "computer" includes all of various devices capable of performing computation and providing the computation result to the user. For example, the computer may include not only a desktop (PC) and a notebook, but also a smart phone, a tablet PC, a cellular phone, a PCS (Personal Communication Service) phone, a mobile terminal of synchronous/asynchronous IMT-2000 (International Mobile Telecommunication-2000), a palm personal computer (PC), and a personal digital assistant (PDA). Further, when a head mounted display (HMD) apparatus includes a computing function, the HMD apparatus may be a computer. Further, the computer may be a server that receives a request from a client and performs information processing.

Hereinafter, embodiments of the inventive concept will be described in detail with reference to the accompanying drawings.

FIG. 1 is a view showing a robot-based surgery system according to a disclosed embodiment.

Referring to FIG. 1, a schematic diagram of the system capable of performing robot-based surgery according to the disclosed embodiment is illustrated.

According to FIG. 1, the robot-based surgery system includes a medical imaging apparatus 10, a server 20, and a controller 30, an imaging unit 36, a display 32, and a surgery robot 34 provided in an operating room.

In one embodiment, the robot-based surgery may be performed by the user controlling the surgery robot 34 using the controller 30. In one embodiment, the robot-based surgery may be performed automatically by the controller 30 without the user control.

The server 20 is a computing device including at least one processor and a communication unit.

The controller 30 includes a computing device including at least one processor and a communication unit. In one embodiment, the controller 30 includes hardware and software interfaces for controlling the surgery robot 34.

The imaging unit 36 includes at least one image sensor. That is, the imaging unit 36 includes at least one camera to image a surgery target portion. In one embodiment, the imaging unit 36 is used in conjunction with the surgery robot 34. For example, the imaging unit 36 may include at least one camera coupled with a surgery arm of the surgery robot 34.

In one embodiment, the image captured by the imaging unit 36 is displayed on the display 32.

The controller 30 receives information necessary for surgery from the server 20 or creates information necessary for surgery and provides the information to the user. For example, the controller 30 displays the created or received information necessary for the surgery on the display 32.

For example, the user controls movement of the surgery robot 34 by manipulating the controller 30 while looking at the display 32 to perform robot-based surgery.

The server 20 creates information necessary for robot-based surgery using medical image data of the object (patient) previously imaged by the medical imaging apparatus 10 and provides the created information to the controller 30.

The controller 30 may display the information received from the server 20 on the display 32 to present the information to the user, or may use the information received from the server 20 to control the surgery robot 34.

In one embodiment, imaging means that may be used in the medical imaging apparatus 10 is not limited particularly. For example, various medical imaging means such as CT, X-Ray, PET, and MRI may be used.

Hereinafter, a method for creating surgical simulation information will be described in detail with reference to the drawings.

Figure 2:
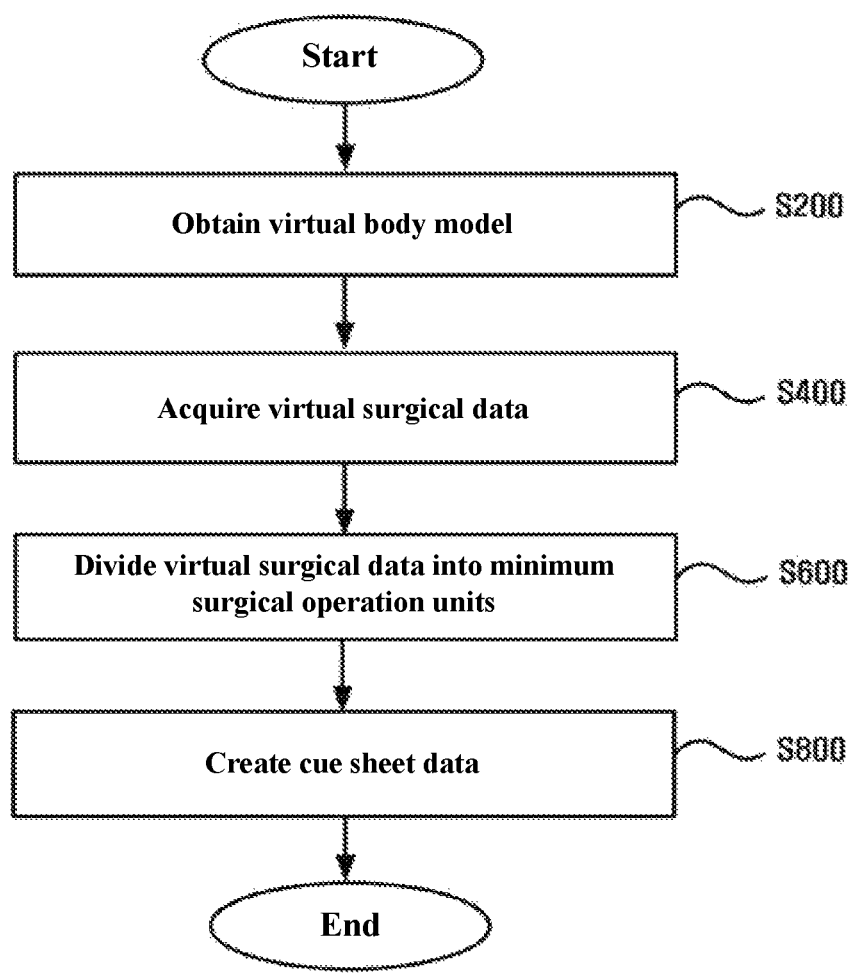
FIG. 2 is a flowchart showing a method for creating surgical simulation information according to one embodiment.

FIG. 2 is a flowchart showing a method for creating surgical simulation information according to one embodiment.

Steps shown in FIG. 2 may be performed in time series by the server 20 or the controller 30 shown in FIG. 1, or may be performed in a computing device provided separately. Hereinafter, for convenience of description, each step is described as being performed by a computer, but a subject to perform each step is not limited to a specific device. All or some of the steps may be performed by the server 20 or the controller 30 or may be performed by a separate computing device.

Referring to FIG. 2, the surgical simulation information creation method according to an embodiment of the inventive concept may include creating a virtual body model corresponding to a patient's body state during surgery (S200); simulating a specific surgical process for the virtual body model to acquire virtual surgical data (S400); dividing the virtual surgical data into minimum surgical operation units, each unit representing one specific operation (S600); and creating a cue sheet data composed of the minimum surgical operation units to indicate the specific surgical process (S800). Hereinafter, detailed description of each step is as follows.

A computer creates the virtual body model corresponding to the body state of the object (e.g., the patient) during surgery (S200).

In one embodiment, the computer may acquire a medical image including a surgery target portion of the object (e.g., the patient), and may create the virtual body model of the patient by 3D-modeling the acquired medical image.

In order for the user to perform a simulation similar to actual surgery, the 3D modeled data corresponding to the actual physical state of the patient is required.

Conventionally, as medical imaging is performed in a different posture from an actual surgery posture and thus-obtained medical image data is directly 3D-modeled, the simulation before the actual surgery may not properly provide an effect of practicing the actual surgery in advance.

Specifically, in general, an internal organ orientation or an organ shape in an image of the patient captured by the medical imaging apparatus while the patient lies down is different from an internal organ orientation or an organ shape of the object during the actual surgery, due to influence of gravity depending on an angle at which the object lies down. Thus, the same simulation situation as the actual surgery may not be provided.

Further, because a pre-surgery simulation is performed in a state in which a simulation state of the body is inconsistent with a pneumoperitoneum state in which the body is filled with carbon dioxide for laparoscopic surgery or robot-based surgery, the pre-surgery simulation may not properly provide an effect of practicing actual surgery in advance. To solve this problem, it is necessary to create 3D modeled data (i.e., 3D pneumoperitoneum model) corresponding to the actual surgical state.

Figure 3:
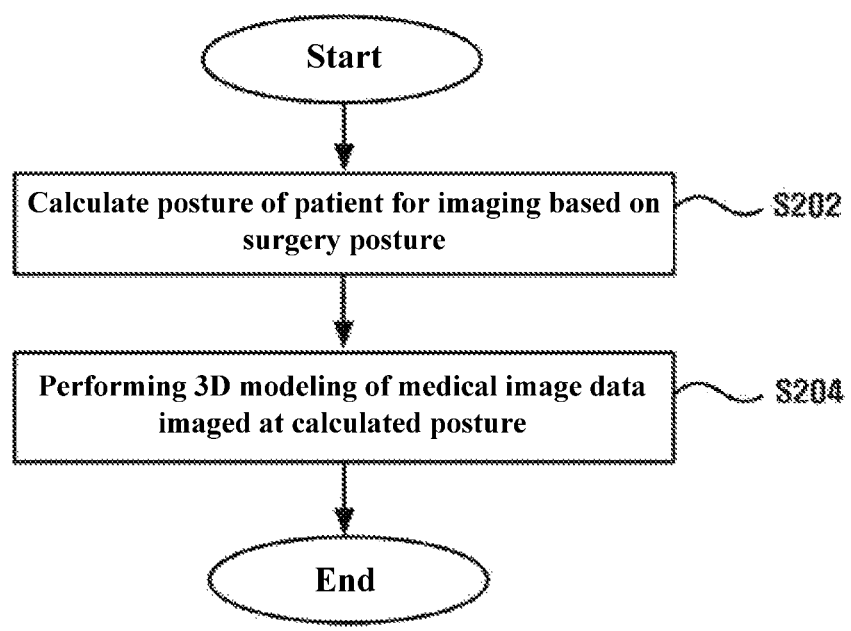
FIG. 3 is a flowchart showing a 3D modeled data creation process via application of a surgery posture according to one embodiment.

FIG. 3 is a flowchart showing a 3D modeled data creation process via application of a surgery posture according to one embodiment.

As one embodiment, as shown in FIG. 3, the computer creates the 3D modeled data based on medical image data captured while applying an actual surgery posture. Specifically, the process may include calculating, by the computer, a posture of the patient at which the patient is imaged, based on a surgery posture determined based on the patient's lesion location or surgery type (S202); and performing, by the computer, 3D modeling of medical image data imaged at the calculated posture (S204).

The computer calculates the posture of the patient at which the patient is imaged, based on the surgery posture determined based on the patient's lesion location or surgery type (S202). The surgery posture may vary depending on the patient's lesion location (i.e., a surgical site), the type of surgery thereof, and the like. The computer calculates the posture for medical imaging to be identical with the patient's surgery posture.

For example, when an upper body of the patient is subjected to surgery while the patient's body is inclined at 15 degrees, the computer may calculate, as the posture for imaging, a posture at which the patient's back is supported on a support such that only the upper body thereof is inclined at 15 degrees. When the posture for imaging is set to the posture at which only the upper body thereof is inclined at 15 degrees, a surgery target portion may be imaged at a posture identical with a surgery posture during actual surgery using the medical imaging apparatus (e.g., a CT apparatus).

Further, for example, the medical imaging apparatus may include a function of adjusting an orientation of the patient body to implement the posture for imaging identical with the surgery posture. For example, when the medical imaging apparatus is the computed tomography (CT) apparatus, a table of the CT apparatus may be tilted or rotated by a predetermined angle in a predetermined direction, and a gantry thereof may be inclined by a predetermined angle in a predetermined direction.

Thus, the computer or the user may control the table and the gantry of the medical imaging apparatus to be tilted at an angle corresponding to the surgery posture. The computer may acquire, from the medical imaging apparatus, the medical image data captured at the posture for imaging at which the body is inclined at an angle equal to a an inclination during the actual surgery.

Further, the computer may receive the patient's surgery posture from the medical staff, and may directly calculate the surgery posture at which the surgery is performed based on the patient's lesion location, the type of surgery thereof, and the like.

Then, the computer acquires the 3D modeled data as created based on the medical image data imaged at the posture for imaging (S204). The computer may create the 3D modeled data by 3D-rendering the 3D medical image of the object. Further, the computer may receive the 3D modeled data created based on the image captured at a specific posture by the medical imaging apparatus. That is, the medical imaging apparatus (e.g., the CT apparatus) may perform 3D rendering of the medical image data, create the 3D modeled data, and transmit the created data to the computer.

Further, in another embodiment, the computer may apply a correction algorithm that changes medical image data imaged under a general imaging condition to image data corresponding to a body state for a specific surgery to create the 3D modeled data. That is, the computer may apply a body change according to gravity in the tilted state or a body change due to the pneumoperitoneum model resulting from carbon dioxide injection to the medical image data obtained by imaging the patient lying down in a general state, thereby to create the 3D modeled data.

For example, the correction algorithm may be calculated by learning big data created by matching medical image data at a general imaging condition and general body state with body condition data corresponding to surgery at a specific body state and a specific surgery condition. The body state data corresponding to the surgery may include image data imaging an internal organ shape or orientation during actual surgery or image data imaging a body surface for actual surgery.

In one embodiment, when creating a pneumoperitoneum model during laparoscopic surgery or robot-based surgery based on the medical image data (e.g., CT data) imaged under the general condition, the computer may match the patient's medical image data with the body surface data for the actual surgery and construct big data to be learned based on the matching result. The body surface data may be data imaged by a medical staff before the surgery.

For example, the medical staff acquires the body surface data by imaging an abdominal surface deformed by injecting carbon dioxide before performing laparoscopic surgery or robot-based surgery. The computer may learn the big data to create a correction criterion or a correction algorithm to correct 3D modeled data in a general state into pneumoperitoneum model data for laparoscopic surgery or robot-based surgery. Thereafter, when medical image data of a new patient is obtained, the computer may correct the 3D modeled data created based on the medical image data based on the correction criterion or the correction algorithm, thereby to create the pneumoperitoneum model data.

Thus, the computer may create the 3D modeled data corresponding to the body state for surgery of a specific patient and may provide the created data to the user.

Referring back to FIG. 2, the computer obtains the virtual surgical data by simulating a specific surgical process for the 3D modeled virtual body model (S400). The user performs a simulation or rehearsal to perform virtual surgery on the 3D modeled image (i.e., virtual body model). For example, the computer may display virtual surgical tool on the 3D modeled image. The user may control the virtual surgical tool in various ways to perform rehearsal to perform surgery on the 3D modeled image.

The virtual surgical data is created by the user simulating surgery on the 3D modeled virtual body model of the patient. The process of acquiring the virtual surgical data may be a process in which the user simulates surgery or in which the user performs rehearsal under the same condition immediately before the actual surgery. The computer may receive the virtual surgical data from the user in various ways.

In one embodiment, the computer may provide the virtual body model to the user through a virtual reality (VR) device, and may input the surgical operation for the virtual body model through the controller. The controller may be implemented in various forms to recognize movement of the user's hand. For example, as the controller is embodied in a glove-like shape, detailed finger movement of the user during the surgery and real-time orientation of a hand thereof may be obtained.

Specifically, the computer provides the virtual body model to a HMD apparatus worn by the user. The computer rotates or enlarges the virtual body model according to the user's manipulation and provides the rotated or enlarged virtual body model to the user. Accordingly, the user performs surgery planning and simulation while examining in detail the virtual body model implemented in the same way as that a body model for the actual surgery scheduled for the patient.

For example, blood vessels and organs that are to be subjected to actual surgery may not be visible to the user due to fat such as omentum (serous membrane), depending on body characteristics of the object. In modeling, the omentum may be removed such that the user may accurately know a location and a shape of the actual blood vessel and organ. Accordingly, the user may establish an optimal surgery plan to reach a surgery target portion for the actual surgery. The computer acquires an input that specific surgical tool is selected by the user, and acquires, through the controller, user manipulation to perform surgery on a specific area of the virtual body model using the corresponding surgical tool.

Further, in one embodiment, the virtual surgical data may include image data imaging implementation of a surgical operation performed by the user on the virtual body model. The computer may create a simulation image based on real-time motion data acquired by the controller, the surgical tool having the motion, and a position in the virtual body model to which the tool moves via the motion.

Further, in another embodiment, the virtual surgical data may be modeling data for the virtual body model itself, and a collection of surgical tool and motion data used at each time in a simulation or rehearsal process. That is, the virtual surgical data may be a plurality of data sets that an external computer may receive and which may allow implementing a simulation image.

The computer divides the virtual surgical data into minimum surgical operation units, each unit representing one specific operation (S600).

The surgery process refers to a process in which a series of surgical operations are performed on the surgery target portion using the surgical tool. Therefore, the virtual surgical data obtained by simulating a specific surgical process includes a series of surgical operations.

That is, the computer may divide the virtual surgical data including a series of surgical operations into the minimum surgical operation units, the minimum unit meaning one specific operation. In this connection, the minimum surgical operation unit refers to a minimum operation unit that may be expressed as a specific surgical operation among a series of surgical operations constituting the entire surgical process. That is, the minimum surgical operation unit may be a detailed surgical operation representing one specific surgical operation.

In this connection, one specific detailed surgical operation may be composed of consecutive operations having the same pattern for the surgical tool or the surgery target portion. In other words, when the virtual surgical data includes a first detailed surgical operation and a second detailed surgical operation, the first detailed surgical operation and the second detailed surgical operation may have different operation patterns. Accordingly, the computer may recognize a time point corresponding to information different from information corresponding to a current time point based on information corresponding to each of time points of the virtual surgical data, and determine whether an operation pattern at the recognized time point is different from that of a detailed surgical operation at the current time point.

In one embodiment, the computer may recognize whether a specific event occurs based on the virtual surgical data, and may recognize the minimum surgical operation unit based on the recognized specific event and thus may divide the virtual surgical data into at least one minimum surgical operation unit.

For example, the computer may recognize change in the surgical tool or the surgery target portion (e.g., an organ such as a liver, a stomach, a blood vessel, a tissue, etc.) based on information included in the virtual surgical data at each time point of the virtual surgical data, and may determine whether an event occurs based on the change. That is, the computer may recognize whether an event occurs based on operation change of the surgical tool, recognize whether an event occurs based on state change of the surgery target portion, or recognize whether an event occurs based on whether change state of the surgery target portion occurs as the operation change of the surgical tool occurs.

For example, the computer may recognize whether an event has occurred based on change in a position, an orientation, a movement degree, a type, etc. of the surgical tool. Upon the determination that the event has occurred, the computer may determine whether operations as performed by the surgical tool at before and after an event occurrence time are different from each other. When the operations as performed by the surgical tool at before and after the event occurrence time are different from each other, each of the operation before the event occurrence time and the operation after the event occurrence time may constitute each detailed surgical operation as the minimum surgical operation unit.

Alternatively, the computer may recognize whether an event has occurred based on change in a position, an orientation, a state, etc. of the surgery target portion. Upon the determination that the event has occurred, the computer may determine whether the surgery target portions before and after an event occurrence time are different from each other. If so, each of an operation before the event occurrence time and an operation after the event occurrence time may constitute each detailed surgical operation as the minimum surgical operation unit.

Alternatively, the computer may recognize whether an event has occurred based on whether the surgical tool contacts the surgery target portion or change in the surgery target portion due to presence or absence of energy of the surgical tool occurs. Upon the determination that the event has occurred, the computer may determine whether surgery operation patterns before and after an event occurrence time are different from each other. If so, each of an operation before the event occurrence time and an operation after the event occurrence time may constitute each detailed surgical operation as the minimum surgical operation unit.

Alternatively, the computer may recognize whether an event has occurred based on whether bleeding has occurred in the surgery target portion. Upon the determination that the event has occurred, the computer may determine whether surgery operation patterns before and after an event occurrence time are different from each other. If so, each of an operation before the event occurrence time and an operation after the event occurrence time may constitute each detailed surgical operation as the minimum surgical operation unit.

Further, according to an embodiment of the inventive concept, the virtual surgical data may be divided to the detailed surgical operations (that is, a minimum surgical operation units) based on whether the event occurs, as described above. However, the present disclosure is not limited thereto. The virtual surgical data may be divided to the detailed surgical operations (that is, a minimum surgical operation units) based on many other criteria.

For example, the virtual surgical data may be divided to the detailed surgical operations based on surgery types (e.g., laparoscopic surgery, robot-based surgery), anatomical body parts where surgery is performed, surgical tools as used, a number of surgical tools, an orientation or a position of the tool displayed on a screen, movement of the surgical tool (for example, forward/reward movement), etc.

The division criteria and detailed categories included within the division criteria may be directly set by the medical staff learning the actual surgery data. The computer may perform supervised learning based on the division criteria and the detailed categories set by the medical staff to divide the virtual surgical data into the detailed surgical operations as a minimum operation unit.

Further, the division criteria and detailed categories included within the division criteria may be extracted via learning of a surgical image by the computer. For example, the computer may calculate the division criteria and detailed categories included within the division criteria via deep learning (i.e., unsupervised learning) of actual surgery data accumulated as big data. Subsequently, the computer may divide the virtual surgical data based on the division criteria created via the learning of the actual surgery data to create the cue sheet data.

Further, in another embodiment, the virtual surgical data or actual surgery data may be divided based on a result of determining whether the virtual surgical data or actual surgery data satisfies the division criterion via image recognition. That is, the computer may recognize the anatomical organ position on the screen, the number of surgical tools appearing on the screen, and the number of the surgical tools on the screen within the image of the virtual surgical data or actual surgery data as the division criterion and may divide the virtual surgical data or actual surgery data into the detailed surgical operation units based on the recognized division criterion.

Further, in another embodiment, the computer may perform the division process for cue sheet data creation based on surgical tool movement data included in the actual surgery data or the virtual surgical data. The actual surgery data may include various information input in a process of controlling the surgery robot, such as the type and the number of surgical tools selected by the user, information about the movement of each surgical tool when the user performs robot-based surgery. The virtual surgical data may include information on the type and the number of surgical tools selected by the user, and movement of each surgical tool during the simulation of the virtual body model. Accordingly, the computer may perform division based on information included in the actual surgical data or virtual surgical data at each time point thereof.

Further, in one embodiment, the virtual surgical data or actual surgery data includes various types of actions such as ablation and suture. Division is performed based on the division criteria. Specifically, a process of dividing the actual surgical data (for example, actual surgery image) about the actual gastric cancer surgery or the virtual surgical data about the simulation of the gastric cancer surgery into detailed surgical operations to create the cue sheet data is as follows.

For example, gastric cancer surgery includes an action to ablate a portion or an entirety of a stomach containing a tumor, and an action to ablate a lymph node. In addition, various resections and connections are used depending on a state of the gastric cancer. In addition, each action may be divided into a plurality of detailed actions based on a specific location where the action is taken and a direction of movement of the surgical tool.

For example, the detailed operation of the gastric cancer surgery may be divided into an opening step, an ablation step, a connection step, and a suture step.

Further, a method of changing a disconnected state of an organ to a connected state includes an in vitro anastomosis method of incising and connecting at least 4 to 5 cm of an end of an anticardium, and an in vivo anastomosis method in which about 3 cm of umbilicus is incised and incision and anastomosis occur in an abdominal cavity. The above-described connection step may be divided in detailed substeps according to the specific connection method as described above.

Furthermore, each surgery operation may be divided into a plurality of detailed surgical operations according to the position and the movement of the surgical tool.

The computer creates the cue sheet data composed of minimum surgical operation units (i.e., detailed surgical operations) and representing a specific surgical process (S800). That is, the computer may sequentially combine the at least one minimum surgical operation unit in a corresponding manner to the specific surgical process simulated using the virtual body model to create the cue sheet data.

According to one embodiment of the inventive concept, each of the divided detailed surgical operations (i.e., minimum surgical operation units) has a standardized name allocated thereto based on a location where the detailed surgical operation is performed and a pathway of the surgical tool.

In one embodiment, the standardized name may be variously defined. For example, when dealing with a specific portion as a lower right portion of the stomach, the name of the portion may be a name commonly used in the medical field. More comprehensive or detailed names defined in the system according to the disclosed embodiment may be used.

Therefore, the rehearsal image may be organized into information in a form of a cue sheet in which a plurality of actions are sequentially arranged based on the standardized names. Similarly, the surgery image about the surgery performed by the user may be divided into action units, and may be organized into cue sheet information.

Further, in one embodiment, the cue sheet data may be created as code data of specific digits based on the division criteria for dividing the surgical data into the detailed surgical operations. That is, the computer divides the virtual surgical data into standardized detailed surgical operations by applying standardized division criteria and designating detailed categories within the division criteria. The computer may allocate a standardized code value to each detailed category and allocate standardized code data to distinguish each detailed surgical operation.

The computer allocates, to each detailed surgical operation, digitalized code data obtained by allocating numbers or letters to categories in order from a higher category to a lower category to which the specific detailed surgical operations belong, according to the order of application of the division criteria. Thus, the computer may create cue sheet data in a form in which not images of the divided detailed surgical operations but the standardized code data of the detailed surgical operations are listed. Further, the user may share or deliver the simulated surgical process by providing only the cue sheet data composed of the standardized code data.

Further, in one embodiment, the computer may allocate a standardized name to a standardized code of each detailed surgical operation. Thus, the user may select and identify only a desired surgical operation (or action) within the entire cue sheet. Further, in this case, the user may easily grasp a progress of the surgery or the rehearsal by simply viewing the cue sheet in which actions are sequentially arranged based on the standardized names thereof, without viewing an entirety of the rehearsal or surgery image.

The cue sheet data may be converted into a surgical image using an image database for each detailed surgical operation. In the image data base, an image matching each code data may be stored. A plurality of images matching each code data may be stored therein depending on a situation. For example, specific detailed code data may include different detailed surgical operation images in the image database according to previously performed operations.

Further, as each cue sheet data is matched with a specific virtual body model and the matching result is stored, the computer may reproduce the cue sheet data as a surgical simulation image by sequentially applying the detailed surgical operations included in the cue sheet data to the virtual body model.

Therefore, the image corresponding to the cue sheet may be reproduced in the same point of view as that of the surgery rehearsal image. Alternatively, the image corresponding to the cue sheet may be reconstructed in a point of view different from that of the surgery rehearsal image and the reconstructed image may be reproduced. Alternatively, the image may be modeled in a 3D manner, and thus the viewpoint and a position thereof may be adjusted according to the user's manipulation.

Figure 4:
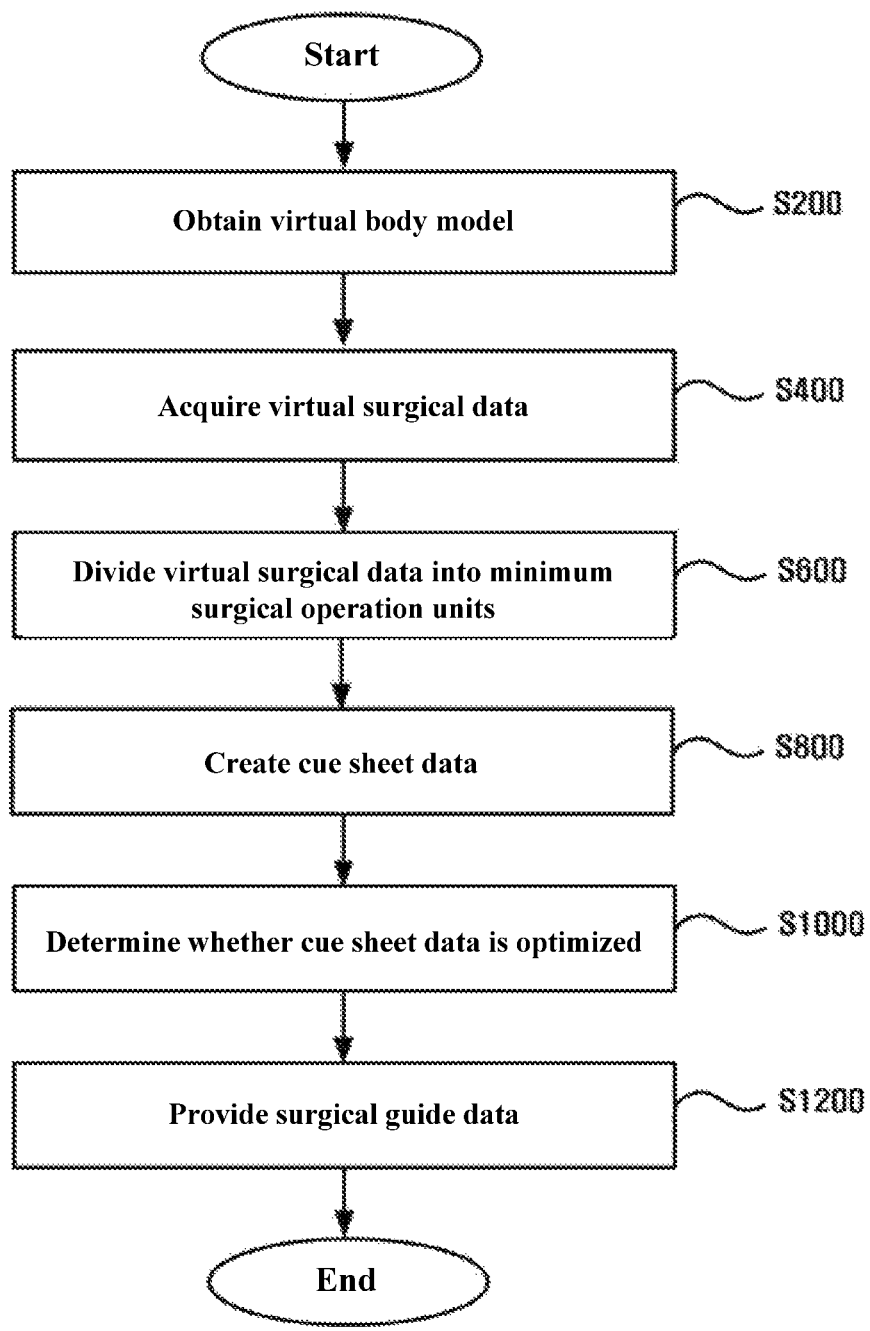
FIG. 4 is a flowchart showing a method for creating surgical simulation information according to another embodiment.

Further, as shown in FIG. 4, in another embodiment, the method may further include determining, by the computer, whether to-be-executed cue sheet data as created based on the user's virtual surgical data is optimized (S1000).

The computer determines adequacy of the to-be-executed cue sheet data via comparison between the to-be-executed cue sheet data and optimized cue sheet data. For example, the computer may determine whether an unnecessary detailed surgical operation that delays a surgery time is contained in the to-be-executed cue sheet data created based on the simulation result by the user, and whether a detailed surgical operation that must be contained before or after a specific detailed surgical operation when performing the specific detailed surgical operation is absent in the to-be-executed cue sheet data. Thus, the computer may determine whether the to-be-executed cue sheet data has been created in a proper manner to be applied to actual surgery of the patient.

The computer may perform a process of calculating optimized cue sheet data to perform evaluation of the to-be-executed cue sheet data.

Figure 5:
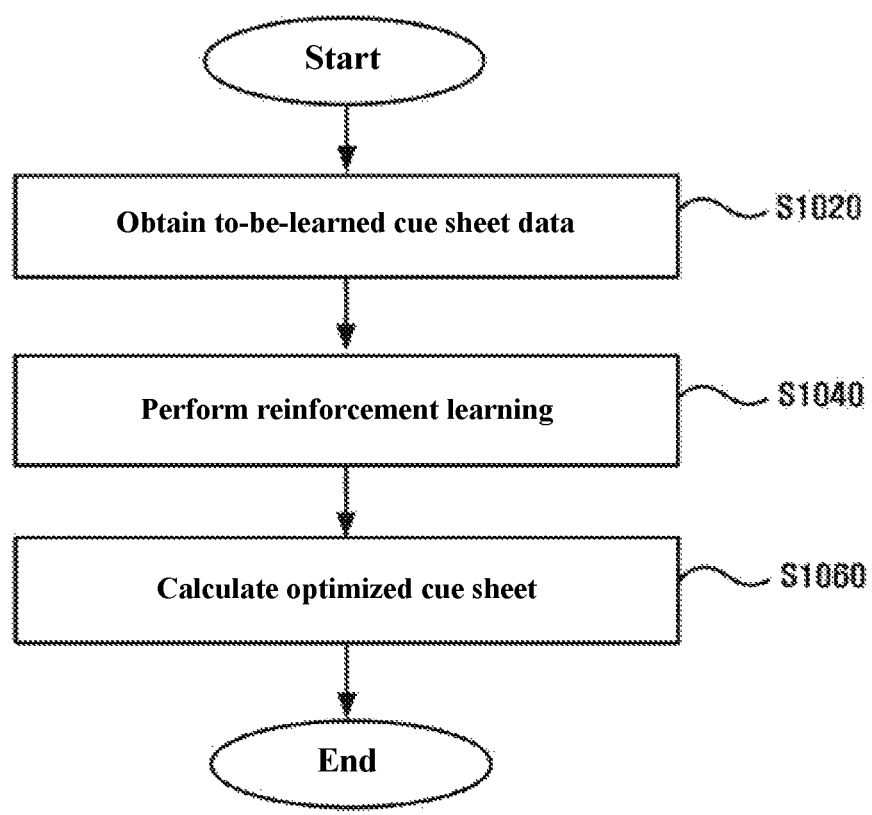
FIG. 5 is a flowchart showing a surgical process optimizing method according to one embodiment.

FIG. 5 is a flowchart showing a surgical process optimizing method according to one embodiment.

The computer acquires one or more to-be-learned cue sheet data (S1020). The to-be-learned cue sheet data refers to learning target data that is to be learned for calculation of the optimized cue sheet data. The to-be-learned cue sheet data may include cue sheet data created based on the actual surgery data (i.e. actual surgery cue sheet data) or cue sheet data created based on the simulated virtual surgical data for reference (i.e. referenced virtual surgery cue sheet data). The actual surgery cue sheet data is created by the computer dividing the actual surgery data according to the division criteria. The referenced virtual surgical cue sheet data is not obtained in the user's surgery simulation process, but is created by performing simulation for purpose of constructing the learning target data or providing the same to practitioners for reference.

Thereafter, the computer performs reinforcement learning using the to-be-learned cue sheet data (S1040). The reinforcement learning refers to one area of the machine learning, and refers to a method in which an agent defined in a certain environment recognizes a current state and selects an action or a sequence of actions that maximizes reward among selectable actions or sequences thereof. The reinforcement learning may be summarized as learning of a scheme of maximizing compensation based on state transition and compensation according to the state transition.

Then, the computer calculates the optimized cue sheet data using the reinforcement learning result (S1060). The optimized cue sheet data is calculated based on the shortest surgical time that may reduce the patient's anesthesia time, a minimum bleeding amount, an essential operation group, and an essential performance sequence, etc. based on the reinforcement learning result.

The essential operation group refers to a group of detailed surgical operations that must be performed together to perform a specific detailed surgical operation. The essential performance sequence refers to a surgical operation sequence at which that operations must be sequentially performed in a course of performing specific surgery. For example, surgical operations that must be performed sequentially and an order thereof may be determined according to the type of surgery or the type of the surgical operation.

Further, the computer may calculate situation-based optimized cue sheet data based on the patient's physical condition, the surgery target portion (e.g., tumor tissue) condition (e.g., a size, a location, etc. of the tumor) thereof via the reinforcement learning. To this end, the computer utilizes the patient condition, the surgery target portion condition, and the like along with the to-be-learned cue sheet data for learning.

In one embodiment, the computer may perform virtual simulation surgery on its own. For example, the computer may create a surgical process according to the type of surgery and the type of the patient based on the disclosed surgical process optimizing method, and may perform the virtual surgery simulation based on the created surgical process.

The computer evaluates results of the virtual surgery simulation. The computer may perform the reinforcement learning based on virtual surgical simulation information and evaluation information on the result thereof, thereby to obtain an optimized surgical process.

A model trained to create the optimal surgical process may not create an optimized surgical process according to an individual patient and a type of surgery thereof because in actual surgery, body structures and types of surgery of patients are different from each other.

Therefore, the computer may create a surgical process based on the patient's body structure and the type of surgery thereof using the trained model, and may perform virtual surgery simulation, based on the created surgical process. In this way, the computer may create an optimized surgical process for an individual patient and a type of surgery thereof via the reinforcement learning.

Further, as shown in FIG. 4, in another one embodiment, the method may further include providing, by the computer, surgery guide data based on specific cue sheet data according to the user's request (S1200). That is, the computer may provide the user with the cue sheet data created by the user performing the simulation or rehearsal during surgery.

Figure 6:
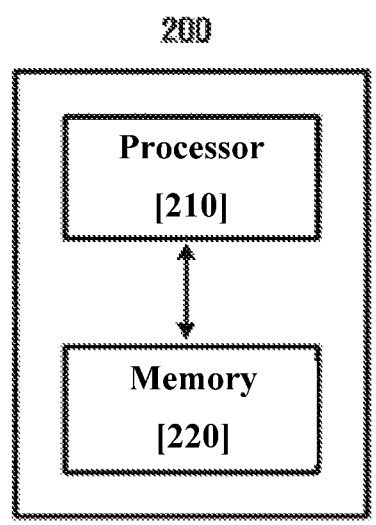
FIG. 6 is a diagram schematically showing a configuration of a device for performing a surgical simulation information creation method according to one embodiment of the inventive concept.

FIG. 6 is a diagram schematically showing a configuration of a device 200 for performing a surgical simulation information creation method according to one embodiment of the inventive concept.

Referring to FIG. 6, a processor 210 may include one or more cores (not shown), a graphics processing unit (not shown) and/or a connection path (for example, a bus, etc.) for communicating signals with other components.

The processor 210 according to one embodiment performs one or more instructions stored in a memory 220 to perform the surgical simulation information creation method as described with reference to FIG. 2 to FIG. 5.

In an example, the processor 210 may execute one or more instructions stored in the memory 220 to create the virtual body model corresponding to the patient's body state for surgery, to obtain the virtual surgical data by simulating a specific surgical process for the virtual body model, to divide the virtual surgical data into the minimum surgical operation units, each unit representing one specific operation, and to create the cue sheet data composed of the minimum surgical operation units and indicating the specific surgical process.

In one example, the processor 210 may further include RAM (Random Access Memory) (not shown) and ROM (Read-Only Memory) (not shown) temporarily and/or permanently storing therein a signal (or data) processed inside the processor 210. Further, the processor 210 may be implemented in a form of a system on chip (SoC) including at least one of a graphic processing unit, RAM, and ROM.

In the memory 220, programs (one or more instructions) for processing and controlling functions by the processor 210 may be stored. The programs stored in the memory 220 may be divided into a plurality of modules according to functions.

The surgical simulation information creation method according to one embodiment of the inventive concept as described above may be implemented using a program (or application) to be executed in combination with a computer as hardware and stored in a medium.

The program may include codes coded in computer languages such as C, C++, JAVA, and machine language that a processor (CPU) of the computer may read through a device interface thereof, in order for the computer to read the program and execute methods implemented using the program. The code may include a functional code related to a function defining functions required to execute the methods, and an execution procedure-related control code necessary for the processor of the computer to execute the functions in a predetermined procedure. Moreover, the code may further include a memory reference-related code indicating a location (address) of an internal memory of the computer or an external memory thereto in which additional information or media necessary for the processor to execute the functions is stored. Moreover, when the processor of the computer needs to communicate with any other remote computer or server to execute the functions, the code may further include a communication-related code indicating how to communicate with any other remote computer or server using a communication module of the computer, and indicating information or media to be transmitted and received during the communication.

The storage medium means a medium that stores data semi-permanently, rather than a medium for storing data for a short moment, such as a register, a cache, or a memory, and that may be readable by a machine. Specifically, examples of the storage medium may include, but may not be limited to, ROM, RAM, CD-ROM, a magnetic tape, a floppy disk, and an optical data storage device. That is, the program may be stored in various recording media on various servers to which the computer may access or on various recording media on the user's computer. Moreover, the medium may be distributed over a networked computer system so that a computer readable code may be stored in a distributed scheme.0

The steps of the method or the algorithm described in connection with the embodiments of the inventive concept may be implemented directly in hardware, a software module executed by hardware, or a combination thereof. The software modules may reside in random access memory (RAM), read only memory (ROM), erasable programmable ROM (EPROM), electrically erasable programmable ROM (EEPROM), a flash memory, a hard disk, a removable disk, CD-ROM, or any form of a computer readable recording medium well known in the art.

According to the disclosed embodiments, the surgical simulation information optimized for each patient is created using previously obtained information and is provided to the surgeon during surgery to assist the surgery.

The effects of the inventive concept are not limited to the effects mentioned above. Other effects not mentioned will be clearly understood by those skilled in the art from the above description.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for creating surgical simulation information by a computer, the method comprising:

creating a virtual body model corresponding to a body state of a patient for surgery;

simulating a specific surgical process on the virtual body model to obtain virtual surgical data;

dividing the virtual surgical data into minimum surgical operation units, each unit representing one specific operation;

creating cue sheet data composed of the minimum surgical operation units, wherein the cue sheet data represents the specific surgical process;

determining whether the created cue sheet data is optimized; and providing surgical guide data based on the cue sheet data determined to be optimized, wherein the determining whether the created cue sheet data is optimized comprises:

obtaining optimized cue sheet data; and comparing the created cue sheet data with the optimized cue sheet data, by determining whether an unnecessary detailed surgical operation that delays a surgery time is contained in the created cue sheet data, and determining whether a detailed surgical operation that must be contained before or after a specific detailed surgical operation when performing the specific detailed surgical operation is absent in the created cue sheet data.

2. The method of claim 1, wherein the dividing of the virtual surgical data into the minimum surgical operation units includes:

recognizing whether a specific event has occurred based on the virtual surgical data; and recognizing the minimum surgical operation units based on the specific event, wherein the specific event includes change in at least one of surgical tool and a surgery target portion included in the virtual surgical data.

3. The method of claim 2, wherein the recognizing of whether the specific event has occurred includes:

recognizing whether the event has occurred, based on change in an operation of the surgical tool;

recognizing whether the event has occurred, based on change in a state of the surgery target portion; or recognizing whether the event has occurred, based on whether change in a state of the surgery target portion occurs as change in an operation of the surgical tool occurs.

4. The method of claim 1, wherein the creating of the cue sheet data includes sequentially combining the minimum surgical operation units in a corresponding manner to the specific surgical process, thereby to create the cue sheet data.

5. The method of claim 1, wherein the creating of the virtual body model includes:

obtaining a medical image including a surgery target portion of the patient; and 3D-modeling the obtained medical image to create the virtual body model.

6. The method of claim 5, wherein the creating of the virtual body model further includes:

calculating a posture of the patient at which the patient is imaged, based on a surgery posture determined based on a lesion location or a surgery type of the patient;

controlling a medical imaging apparatus to adjust an orientation of a body of the patient to implement the calculated posture, which is identical with the surgery posture;

controlling the medical imaging apparatus to capture the medical image of the patient with the calculated posture; and 3D-modeling the virtual body model by correcting the medical image based on the captured medical image of the patient with the calculated posture.

7. The method of claim 1, wherein the obtaining of the optimized cue sheet data includes:

obtaining one or more to-be-learned cue sheet data;

performing reinforcement learning using the one or more to-be-learned cue sheet data; and obtaining the optimized cue sheet data based on the reinforcement learning result.

8. A non-transitory computer readable medium storing a computer program, and coupled with a computer hardware, to create surgical simulation information, wherein the computer program is configured to perform the method of claim 1.

9. A device comprising:

a memory for storing one or more instructions; and a processor configured to execute the one or more instructions stored in the memory, wherein the processor is configured to execute the one or more instructions to:

create a virtual body model corresponding to a body state of a patient for surgery;

simulate a specific surgical process on the virtual body model to obtain virtual surgical data;

divide the virtual surgical data into minimum surgical operation units, each unit representing one specific operation;

create cue sheet data composed of the minimum surgical operation units, wherein the cue sheet data represents the specific surgical process;

determine whether the created cue sheet data is optimized; and provide surgical guide data based on the cue sheet data determined to be optimized, wherein the processor is further configured to, in determining whether the created cue sheet data is optimized comprises:

obtain optimized cue sheet data; and compare the created cue sheet data with the optimized cue sheet data, by determining whether an unnecessary detailed surgical operation that delays a surgery time is contained in the created cue sheet data, and determining whether a detailed surgical operation that must be contained before or after a specific detailed surgical operation when performing the specific detailed surgical operation is absent in the created cue sheet data.

* * * * *